US009630006B2

(12) United States Patent
Gordon et al.

(10) Patent No.: US 9,630,006 B2
(45) Date of Patent: Apr. 25, 2017

(54) WEARABLE ALARM SYSTEM FOR A PROSTHETIC HEARING IMPLANT

(75) Inventors: Brian Gordon, Chatswood (AU); Roger Leigh, East Ryde (AU); Tadeusz Jurkiewicz, Rozelle (AU); Kiangkai Tankongchumruskul, Warrimoo (AU)

(73) Assignee: Cochlear Limited, Macquarie University, NSW (AU)

( * ) Notice: Subject to any disclaimer, the term of this patent is extended or adjusted under 35 U.S.C. 154(b) by 1337 days.

(21) Appl. No.: 12/535,089

(22) Filed: Aug. 4, 2009

(65) Prior Publication Data

US 2009/0292338 A1 Nov. 26, 2009

Related U.S. Application Data

(62) Division of application No. 11/487,402, filed on Jul. 17, 2006, now Pat. No. 7,571,006.

(30) Foreign Application Priority Data

Jul. 15, 2005 (AU) ................................ 2005903755

(51) Int. Cl.
*A61N 1/36* (2006.01)
(52) U.S. Cl.
CPC .............................. *A61N 1/36032* (2013.01)
(58) Field of Classification Search
CPC .............. A61N 1/36046; A61N 1/0541; A61N 1/36032; A61F 11/04
USPC ........................................ 607/55, 57, 60, 63
See application file for complete search history.

(56) References Cited

U.S. PATENT DOCUMENTS

| 4,297,677 A | * | 10/1981 | Lewis et al. ................... 340/540 |
| 4,345,336 A | * | 8/1982 | Plastino ............................. 2/414 |
| 4,777,474 A | * | 10/1988 | Clayton .................... 340/539.11 |
| 4,972,491 A | * | 11/1990 | Wilcox, Jr. .................... 381/375 |
| 5,343,532 A | | 8/1994 | Shugart, III |
| 5,420,930 A | | 5/1995 | Shugart, III |
| 5,425,104 A | * | 6/1995 | Shennib ......................... 381/326 |
| 5,584,869 A | * | 12/1996 | Heck et al. ...................... 607/57 |
| 5,867,105 A | * | 2/1999 | Hajel .......................... 340/691.3 |
| 5,941,905 A | * | 8/1999 | Single ............................. 607/57 |
| 6,023,517 A | * | 2/2000 | Ishige ............................ 381/315 |
| 6,067,006 A | | 5/2000 | O'Brien |
| 6,408,468 B1 | | 6/2002 | Comfort |
| 6,782,106 B1 | | 8/2004 | Kong et al. |
| 7,352,871 B1 | * | 4/2008 | Mozo .............................. 381/72 |
| 2004/0049242 A1 | | 3/2004 | Ibrahim |
| 2004/0257233 A1 | | 12/2004 | Proebsting |
| 2005/0281425 A1 | * | 12/2005 | Greuet et al. .................. 381/331 |
| 2008/0025524 A1 | | 1/2008 | Vaudrey et al. |

* cited by examiner

*Primary Examiner* — Christopher D Koharski
*Assistant Examiner* — Roland Dinga
(74) *Attorney, Agent, or Firm* — Hauptman Ham, LLP

(57) ABSTRACT

A prosthetic hearing implant kit is disclosed. The prosthetic hearing implant kit comprises internal components configured to be implanted in a recipient and comprises an internal coil; external components configured to be worn by the recipient and comprises an external coil adapted to be inductively coupled with said internal coil; and an alert system having a second external coil and adapted to receive an external alarm and to transmit signals to said implanted components via said external coil for providing the recipient with a corresponding alarm indication.

34 Claims, 9 Drawing Sheets

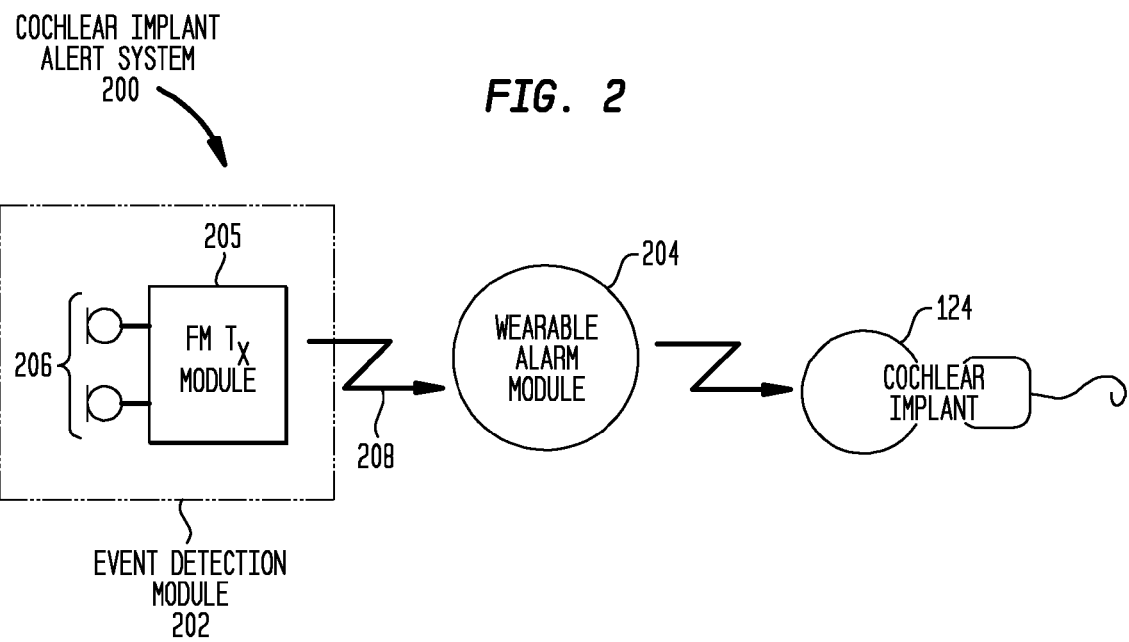

WEARABLE ALARM SYSTEM FOR A PROSTHETIC HEARING IMPLANT

CROSS REFERENCE TO RELATED APPLICATIONS

This application is a divisional of 11/487,402 filed Jul. 17, 2006, which makes reference to and claims the benefit of co-pending Australian Provisional Patent Application No. 2005903755 filed Jul. 15, 2005, each of which is are hereby incorporated by reference herein.

BACKGROUND

Field of the Invention

The present invention relates generally to prosthetic hearing implants and, more particularly, to a wearable alarm system for a prosthetic hearing implant.

Related Art

Door bells, telephones, alarm systems (fire, intruder, smoke etc), alarm clocks, and analogous devices emit acoustic warning signals making them suitable for people having normal hearing. People with severe or profound hearing loss must receive a prosthetic hearing implant such as a cochlear™ prostheses (commonly referred to as cochlear™ prosthetic devices, cochlear™ implants, cochlear™ devices, and the like; simply "cochlear implants" herein), to perceive such sounds.

However, most auditory prosthetic recipients prefer to sleep without wearing the external components of the prosthesis due to the physical shape, size, weight and/or the need for interconnecting cables, which are designed for use by the recipient during normal daily activities. This renders such recipients cut off from external audio input while asleep. This can be very inconvenient if the sound from an alarm clock is not heard or could be potentially dangerous in the event of a fire or intruder alarm not being heard.

Current warning devices for the hearing impaired mostly involve visual notification such as a flashing light to alert the person to the phone ringing, people at the door, or alarms such as smoke alarms. Such a visual alarm is obviously not adequate when asleep. Alarms for sleeping, hearing impaired people exist using vibration, either of the bed or pillow to wake the person. Such alarms can be activated by phone, baby alarms, smoke alarms etc. However, such devices are cumbersome, usually require a power source (with battery as back up only) and are not readily transportable.

Other situations may arise which require the removal of the external device, such as when recipients need to wear a closely fitting helmet. A helmet may need to be worn when riding a bike, motorcycle, when skiing, or even on a building site. Removal of the external device can be dangerous in such situations as the recipients are not able to hear warning signals that alert people in the surrounding area to danger.

SUMMARY

In one aspect of the invention, a prosthetic hearing implant kit is disclosed. The prosthetic hearing implant kit comprises internal components configured to be implanted in a recipient and comprises an internal coil; external components configured to be worn by the recipient and comprises an external coil adapted to be inductively coupled with said internal coil; and an alert system having a second external coil and adapted to receive an external alarm and to transmit signals to said implanted components via said second external coil for providing the recipient with a corresponding alarm indication.

In another aspect of the invention, an alert system for use in a prosthetic hearing implant is disclosed. The alert system for use in a prosthetic hearing implant comprises an event detection module comprising at least one microphone and a transmitter configured to transmit a signal representative of received audio signals; and a wearable alarm module configured to analyze one or more characteristics of said representative signal, and to invoke said prosthetic hearing implant to generate an alarm indication when said representative signal represents a received audio signal constituting an alarm event.

In a further aspect of the invention, a method of communicating an external alarm to the recipient of a prosthetic hearing implant is disclosed. The method of communicating an external alarm to the recipient of a prosthetic hearing implant comprises receiving at an event detection module audio signals; transmitting to a wearable alarm module signals representative of said received audio signals; determining by said wearable alarm module whether said receipt of said audio signals constitutes an alarm condition; and controlling the prosthetic hearing implant to provide the recipient with an alarm indication when said audio signals constitute an alarm condition.

BRIEF DESCRIPTION OF THE DRAWINGS

Illustrative embodiments of the present invention will be described with reference to the accompanying drawings, in which:

FIG. 2 is a schematic block diagram of one embodiment of a cochlear implant alert system showing the alert system integrated into a cochlear implant such as the cochlear implant illustrated in FIG. 1;

DETAILED DESCRIPTION

Introduction

Figure 1:
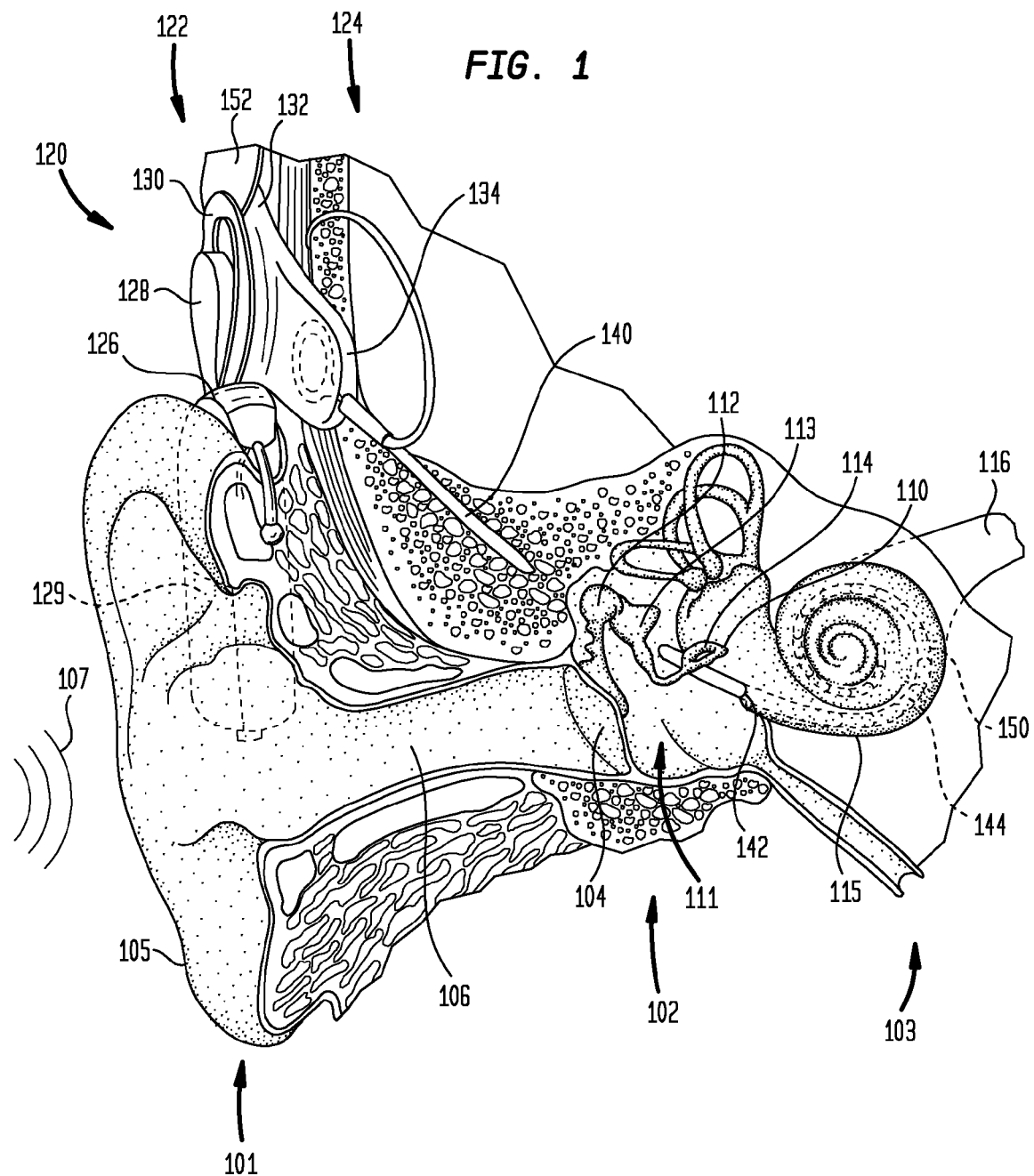
FIG. 1 is a schematic block diagram of an exemplary cochlear implant with which aspects of the present invention may be implemented.

Aspects of the present invention provide an alert system for an implanted hearing prosthesis recipient. The alert system is worn by the recipient in place or in addition to the external components of the hearing prosthesis. Upon receipt of a predefined external alarm the alert system transmits signals which are received by an implanted hearing prosthesis as an alarm indication. The present invention may be utilized, for example, under conditions where it may not be practical for recipients to wear their normal speech processor, such as while in bed sleeping.

In a broad form, the present invention provides an alarm system for communicating an alarm to an implanted hearing prosthesis recipient.

In one aspect, the alarm system is adapted to receive an external alarm and includes means to transmit alarm signals adapted to be detected and received by an implanted hearing prosthesis as an alarm indication, the arrangement being such that when an external alarm is received, the alert system transmits an alarm signal.

In another aspect, the present invention provides a method of communicating an external alarm to the recipient of an implanted hearing prosthesis, including: providing an alarm device adapted to receive an external alarm; upon receiving an external alarm, transmitting said external alarm to said implanted hearing prosthesis as an alarm signal. The alarm device may include an FM receiver, alarm detection, encoder/transmitter functions, an LCD display, user interface, power supply and alarm clock functions. In one embodiment, the alarm device includes only the FM receiver, alarm detection and encoder/transmitter functions. The alarm clock functions are removed and the push button user interface is simplified to just an on/off switch.

The alert system may be configured to respond to any of its alarm inputs and to transmit an encoded alarm stimulus sequence to the cochlear implant to alert the recipient.

The alert system may be powered by battery or other power source such as a capacitor. The alert system may operate with very low standby power until an alarm condition occurs, at which time it sends short duration power and data signals to the implant. In this way, the power requirements, physical size and weight of the device can be minimized.

The alert device may be made up from a transmitter module and a receiver module. Preferably, the receiver module includes an FM wireless receiver linked to a remote FM wireless microphone that picks up environmental sounds and specifically, sounds that the cochlear implant recipient needs to be alerted about. The alert device could then be programmed to respond only to sustained sounds of sufficient loudness to be classified as alarms. Such sounds could include an alarm clock, door bell, telephone or fire or intruder alarm. The alert system may also be configured to respond to a baby monitor if a wireless microphone was placed close to the loudspeaker of the monitor. The FM wireless microphone system is preferably a standard commercially available system of the type typically used by hearing impaired persons to augment their hearing prosthesis. FM wireless receivers systems are now available as low power, single chip devices, facilitating easy integration into custom electronic devices. By making it compatible with existing FM systems the alert device can become more affordable and easier to use.

In one embodiment, the alert system may be easily and securely attached while being relatively unobtrusive to the wearer. Present commercially available alarm monitoring/alerting systems are relatively large and bulky and use vibratory "bed shakers" as the alerting means. Embodiments of the present invention require only a small head-worn device in addition to the wireless microphone that many recipients will already be using.

In one embodiment, the wearable alarm device is entirely self-contained in a single head worn assembly and operates in conjunction with a commercially available wireless microphone. It may include a digital alarm clock, LCD display, programmable alarm selection and a programmable power and data encoder that allows presetting the type of electrical stimulus that is sent to the implant to represent the alarm sound sounds. In this instance, the holding means may be a combination of magnetic forces and a soft elastomeric layer on the bottom surface of the coil to securely locate the device on the head.

Alternatively, the transmitter module that couples to the prosthesis is a separate component and is made of very thin and flexible material allowing it to be worn unobtrusively under a light weight headband. This coil configuration would typically not use a magnet for attachment since the magnet is a relatively thick and rigid component. In this embodiment, the non-slip coating could be used advantageously on both bottom and top surfaces of the coil to improve its fixation to the head and headband. This part of the alarm device may be fixed to the headband by other means such as a pocket, adhesive, clip or Velcro. The other part of the alarm device, the receiver module, in this case an FM receiver and control functions, are then built into a separate module that can be attached to the front of the headband via a clip or pocket sewn into the headband, etc. The coil may be connected to the control unit by a short, light-weight cable or may even be located separately to the transmitter module. Such a thin and flexible coil also has application for hearing prosthesis recipients who need to wear close fitting helmets for sports and cycling, and can be used in conjunction with the recipient's regular speech processor.

Thus recipients can have the choice of either a single integrated package attached via the magnet and no-slip surface or a headband mounted system or a combination.

The present invention accordingly allows people with a hearing prosthesis to conveniently be alerted to alarms while sleeping or when they are without their external speech processor. This provides a significant advantage to the hearing prosthesis recipient over existing alternatives.

Exemplary Cochlear Implant

In another embodiment, the alert system may be easily and securely attached while being relatively unobtrusive to the wearer. Present commercially available alarm FIG. 1 is a perspective view of an exemplary cochlear implant 120 in which embodiments of the present invention may be advantageously implemented. In fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates tiny hair cells (not shown) that line the inside of cochlea 115. Activation of the hair cells causes appropriate nerve impulses to be transferred through the spiral ganglion cells and auditory nerve 116 to the brain (not shown), where they are perceived as sound. In deaf persons, there is an absence or destruction of the hair cells. A cochlear implant 120 is utilized to directly stimulate the ganglion cells to provide a hearing sensation to the recipient.

FIG. 1 also shows how a cochlear implant 120 is positioned in relation to outer ear 101, middle ear 102 and inner ear 103. Cochlear implant 120 comprises external component assembly 122 which is directly or indirectly attached to the body of the recipient, and an internal component assembly 124 which is temporarily or permanently implanted in the recipient. External assembly 122 comprises several components including a plurality of audio sensors spatially arranged on external components 122 of cochlear implant 120 for detecting sound. The spatial arrangement of the plurality of audio sensors is described in greater detail below.

Sound processor 126 is an directional sound processor configured to generate coded stimulation control signals representing sound detected by the plurality of audio sensors from a desired direction. These coded signals are then provided to an external transmitter unit 128. In the embodiment shown in FIG. 1, sound processor 126 is a behind the ear (BTE) sound processing unit. The BTE is constructed and arranged so that it can fit behind the outer ear 101 of a recipient. BTE may include a power source to power all elements of the cochlear implant, such as the external coil. In certain embodiments, the power source may be physically disconnected from the BTE, thereby causing the BTE to discontinue operation. Furthermore, in other embodiments, accessories can be connected to the BTE to add additional functionality.

It would be appreciated by one of ordinary skill in the art that sound processor 126 may also comprise a body-worn sound processor, a modular sound processor or a sound processor headset. Details of the sound processing performed in sound processor 126 in accordance with embodiments of the present invention are discussed below.

External transmitter unit 128 comprises an external coil 130 and, preferably, a magnet (not shown) secured directly or indirectly in external coil 130. External transmitter unit 128 is configured to transmit the coded signals from sound processor 126, along with power from a power source 129 such as a battery to internal components 124 through tissue 152.

Internal components 124 comprise an internal receiver unit 132 having an internal coil (not shown) that receives and transmits power and coded signals received from external assembly 122 to a stimulator unit 134 to apply the coded signal to cochlear 115 via an implanted electrode assembly 140. Electrode assembly 140 enters cochlea 115 at cochleostomy region 142 and has one or more electrodes 150 positioned to be substantially aligned with portions of tonotopically-mapped cochlea 115. Signals generated by stimulator unit 134 are typically applied by an array 144 of electrodes 150 to cochlea 115, thereby stimulating auditory nerve 116.

FIG. 2 is a functional block diagram of one embodiment of a cochlear implant alert system 200 of the present invention. As noted, alert system 200 generally comprises an event detection module 202 and a wearable alarm module 204, as noted above.

In one embodiment, event detection module 202 is an FM wireless system that comprises sensitive microphone(s) 206 configured for wide-angle, normal or directional sound pick up. This allows event detection module 202 to be either placed centrally in a room such that it picks up all sounds (for example, fire or intruder alarm, telephone, door bell, etc), or alternatively placed next to an alarm or monitoring device to enable preferential detection of acoustic outputs from specific devices (for example, clock radio alarm, baby monitor, mobile phone etc.). Event detection module 202 transmits a signal 208 in response to the presence of an audio signal. In the embodiment shown in FIG. 2A, signal 208 is a wireless signal such as an RF signal.

Wearable alarm module 204 receives signal 208 and determines whether an alarm event has been detected. This is determined by analyzing one or more characteristics of the received signal, such as amplitude, frequency, duration, etc. Alternatively, more sophisticated signal analysis can be performed on the received FM signal to select specific sounds, for example, via an integrated digital signal processor (DSP).

When an alarm event is detected, a transmission to internal components 124 of cochlear implant 120 occurs. The transmission may comprise a predefined burst of encoded RF energy.

Figure 3A:
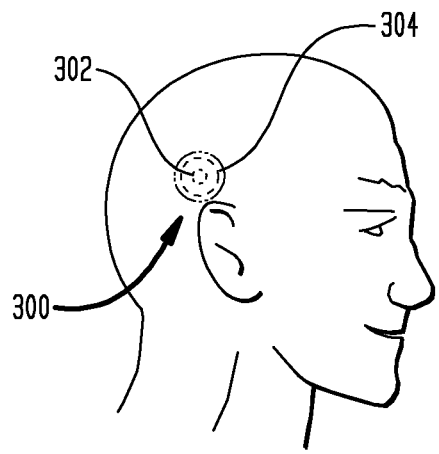
FIG. 3A is a perspective view of one embodiment of a cochlear implant alarm apparatus shown in its operational position so as to interoperate with implanted components of the cochlear implant illustrated in FIG. 1A.
Figure 3B:
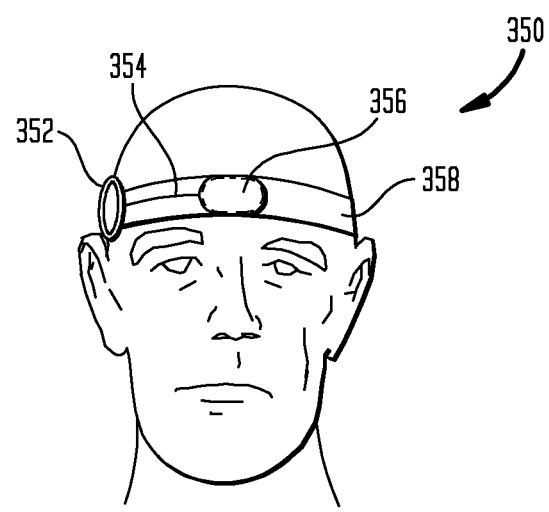
FIG. 3B is a perspective view of another embodiment of a cochlear implant alarm apparatus shown in its operational position so as to interoperate with implanted components of the cochlear implant illustrated in FIG. 1A.

FIGS. 3A and 3B are perspective views of alternative embodiments of the wearable alarm module shown in its operational position on a recipient. As noted, when in the illustrated position, the wearable alarm module interoperates with implanted components 124 of cochlear implant 100.

Wearable alarm module 204 comprises a variety of components described below, including a transmitter coil 304 to be inductively coupled to implanted coil 132 (FIG. 1). The embodiment of wearable alarm module 204 illustrated in FIG. 3A, referred to as wearable alarm generation module 300, is a single integrated unit held in place on the recipient by utilizing rare earth magnets. One magnet 302 is located in wearable alarm module 300 while the other is located in cochlear implanted stimulator/receiver unit 134 (FIG. 1). In one embodiment, such magnets will hold coil 304 in position for an axial separation with internal coil 132 of at least 10 mm and for lateral offsets of at least 6 mm.

The embodiment of alarm module 204 illustrated in FIG. 3B, referred to as alarm generation module 350, comprises two separate components: a separate thin, flexible coil 352 connected via a cable 354 to a control unit 356. These components are removably secured to a light-weight head band 358. Rather than the fully integrated system of FIG. 3A, separate coil 352 may be made very thin and flexible so that it conforms to the shape of the recipient's head. This allows it to be held in position under unobtrusive, lightweight head band 358 that may be comfortably worn during sleep. People readily adapt to wearing such things at night and a head band is far less obtrusive than say a sleep-apnea mask.

Preferably, thin coil 352 does not include a magnet since this increases its thickness and weight. However, the application of a non-slip elastomeric coating to at least the bottom surface of integrated device 300 would be advantageous to ensure coil 352 remains in position.

Another benefit of a thin flexible coil 352 compared to a more conventional rigid coil is that it inherently makes closer contact with the recipient's head. It can also be made somewhat larger in diameter without increasing the bulk of the coil. Both of these attributes may be used to improve the degree of coupling to implant receiver coil 132 and improving the tolerance of the system to coil misalignment. In this embodiment, the remaining components of wearable alarm device 350 are disposed in a separate case that can be made quite small without consideration to the size of the integrated coil. Alternatively, a large flexible coil may be used with a small control box. FM receiver/control unit 356 is attached to headband 358 via a clip, Velcro, or sewn in pocket or any other suitable means. It is not necessary to stabilize its position relative to the recipient's head. Short cable 354 connects coil 352 to control unit 356. In embodiments in which there is an electrical connector to coil 302/352 such connector is preferably located away from the coil itself to avoid the bulk of a connector. This can readily be achieved by fabricating leads 354 to coil 352 using the same flex-PCB process that is used to make the coil 352. The dimensions of coil 352 are approximately 25 mm to 40 mm in diameter and the integrated lead would be approximately 50 mm to 100 mm in length. It should be appreciated that other dimensions are possible given the particular application.

Figure 4:
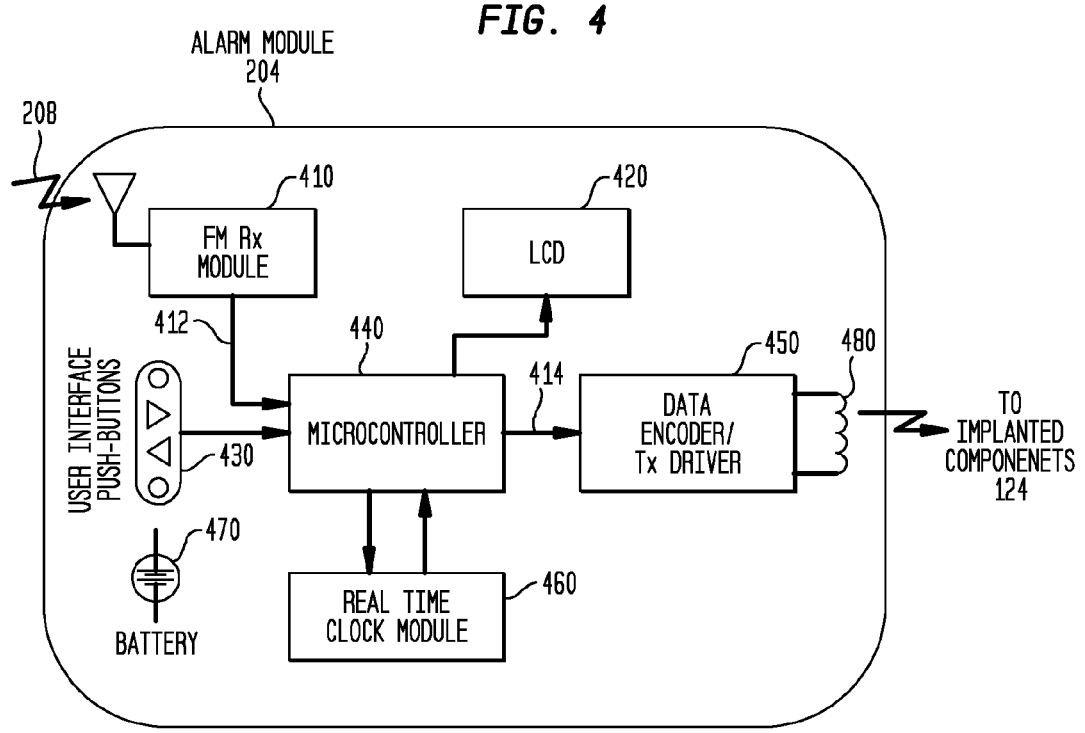
FIG. 4 is a schematic block diagram of the wearable alarm module shown in FIG. 2 in accordance with one embodiment of the present invention.

FIG. 4 is a schematic block diagram of one embodiment of alarm module 204. Wearable alarm module 204 receives signal 208 at an FM receiver module 410. FM receiver module 410 demodulates signal 208 and provides an audio signal 412 to an A/D input of a microcontroller 440. Microcontroller 440 monitors audio signal 412 to detect a signal that exceeds preset energy thresholds, i.e. a combination of signal amplitude and duration. Alternatively, more sophisticated signal analysis can be performed on the received FM signal to select specific sounds, for example, via an integrated digital signal processor (DSP).

When a suprathreshold signal is detected, microcontroller 440 sends control data 414 to the data-encoder and transmitter module 450. This results in the transmission to internal components 124 of cochlear implant 120 of a predefined burst of encoded RF energy via transmitter coil 480. As with external coil 130, transmission coil 480 is inductively coupled to internal coil 132 of cochlear implant 120 when wearable alarm module 204 is properly positioned on the recipient's head. Cochlear implant 100 extracts both power and data from the inductively coupled energy, and outputs the stimulus sequence encoded therein.

The preceding description applies to a cochlear implant that receives both power and data from an external device. Note that alternative cochlear implant architectures include an implanted energy source and/or a stimulus sequence controller. In this case, alert system 200 may send only a data signal to the implanted components of the cochlear implant sufficient to cause it to output a predefined alerting sequence. However, for the purpose of clarification of the present invention, its operation is described assuming a conventional externally powered cochlear implant.

In its simplest form, the predefined data sequence transmitted to internal components 124 is a constant amplitude stimulus sequence directed to one of the active electrodes. Alternatively, it could be a sequence of pulses applied sequentially to a group of predefined electrodes. The object is to create a sound capable of arousing the recipient from the sleeping state. It may be desirable to steadily increase the amplitude of the stimuli over a series of bursts to avoid startling the person from their sleeping state.

Each cochlear implant recipient has unique electrical stimulation parameters so it is necessary to set stimulus levels to suit each recipient of the device. These parameters are typically set up at a cochlear implant clinic during a routine fitting session. Advantageously, alarm system 200 may be set up via the regular programming system and uses the same serial communications port used for programming recipients' speech processors. The recipient is able to select from a range of predefined alarm tones and the stimulus level defaults to a value based on the recipient's "comfort" level, which is known from parameters acquired during the fitting of the speech processor. The default value can then be adjusted up or down as necessary, or the user may have access to the loudness control via the user interface 230 if this is provided. After programming, alarm system 200 becomes personalized to a specific recipient.

It is desirable that alert system 200 is as small and light weight as practicable so that it is minimally obtrusive to the recipient. Although cochlear implants have improved significantly over time and with advances in low power electronics, power consumption remains an issue due to the inherent inefficiency of the inductively coupled RF power/data link. State of the art cochlear implants use high energy density primary cells such as Zinc/air or rechargeable Lithium Ion or Nickel Metal Hydride secondary cells. These cells are small enough to be incorporated into speech processor configurations that can be worn behind the ear (BTE). These devices are very large by hearing aid standards, but users accept this size in preference to having an even larger body-worn device with the associated interconnecting cables to the ear-level components (for example, the microphone and coil). It has not been practical to build a multi-channel cochlear implant speech processor entirely into a self supporting on-the-head (OTH) device due to the size and weight of the batteries that would provide sufficient power to maintain continuous operations for a reasonably acceptable period of time.

However, alert system 200 typically operates in a low power standby mode and draws high power for only relatively short periods of time in response to detection of an alarm condition. For example, a typical cochlear implant draws power of the order of 50 mW while processing and transmitting normal environmental sounds and speech to the implant. This is not the maximum power consumption but is based on a transmission duty cycle of approximately 50%. A power source would need to have a capacity of 400 mWhr to support such a system for 8 hours. This compares to alert system 200 for which the high power duty cycle would be perhaps 1 minute in 8 hours, that is, approx 0.2%, for the wake-up alarm application. Low-power control electronics and FM receiver module 210 would consume approx 1.5 mA or 5 mW from a Lithium battery 470 during the standby state. This translates to approximately 40 mWhr for 8 hours of operation or 10% of a typical cochlear implant. With battery 470 being the largest component of alert system 200), such a substantial reduction in power requirement makes it possible to design a thin and light-weight device.

In one embodiment of the present invention, wearable alarm module 204 further comprises a real-time clock/alarm 460 and an LCD 420. This allows alert system 200 to be used in a limited way, for example, autonomous alarm clock wake-up mode only, independent of event detection module 202. For this mode of operation it is necessary to set up the operating parameters, for example, set time, set alarm clock, alarm on/off, external alarm detection (FM receiver) on/off, alarm sound select, alarm loudness adjust. This is achieved via a user interface (UI) having several pushbuttons that allow the recipient to configure the device. Whilst it is possible to provide access to all of these functions via user interface 430, it may be preferable that these parameters are configured by the audiologist/clinician via the programming system, as described above.

Figure 5A:
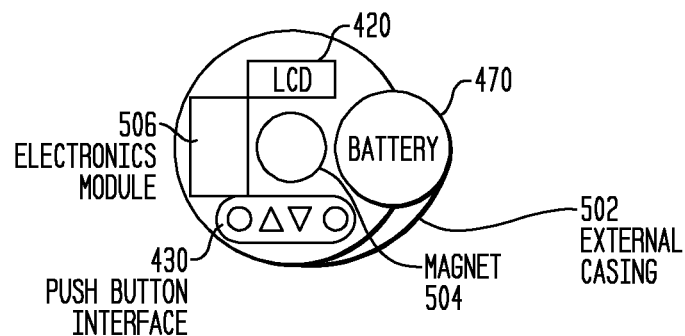
FIG. 5A is the top view of the alarm module showing the layout of the major components and functional modules in accordance with one embodiment of the present invention.
Figure 5B:
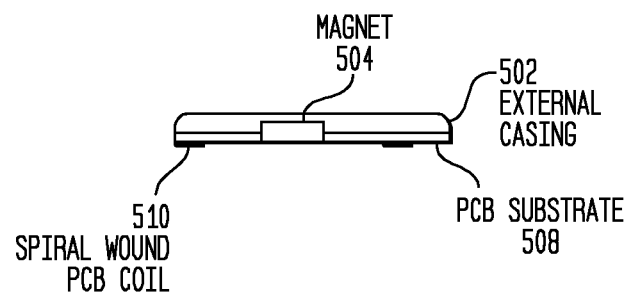
FIG. 5B is a side view of the alarm module of FIG. 5A in accordance with one embodiment of the present invention.
Figure 5C:
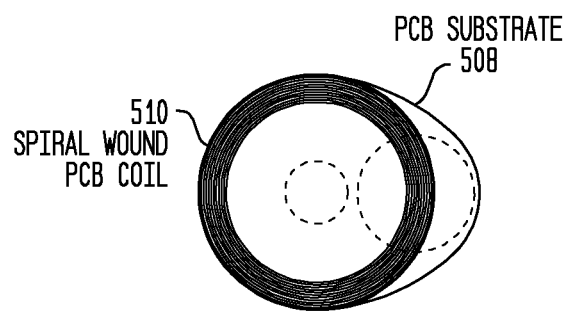
FIG. 5C is a bottom view of the alarm module of FIG. 5A in accordance with one embodiment of the present invention.

FIGS. 5A-5C are top, side and bottom views, respectively, of one embodiment of alarm device 200, referred to herein as alarm device 500, showing the physical layout of the major components of one embodiment of the device. In this illustrative embodiment, the following primary components are shown: LCD display 420, user interface 430, battery 470 and an electronics module 506. In this embodiment, electronics module 502 comprises clock module 460, microcontroller 440, FM receiver module 410, and data encoder/transmitter-driver module 450.

The side and bottom views of FIGS. 5B and 5C show the layout of an embodiment of transmit coil 510. In this embodiment, transmit coil 510 is a spirally wound flat PCB coil. As can be seen, the arrangement of the elements shown in FIGS. 5A-5C minimizes the size of the wearable alarm module 500 of the system.

In addition to the desire for a small and light weight wearable alarm module that is minimally obtrusive to the wearer, alarm modules of the present invention are preferably reliably and securely held on a recipient's head so that they remains relatively fixed in position over an implanted receiver coil. FIGS. 3A and 3B described above are just two methods of holding an alarm module in place, but other fixation means are possible.

Figure 6A:
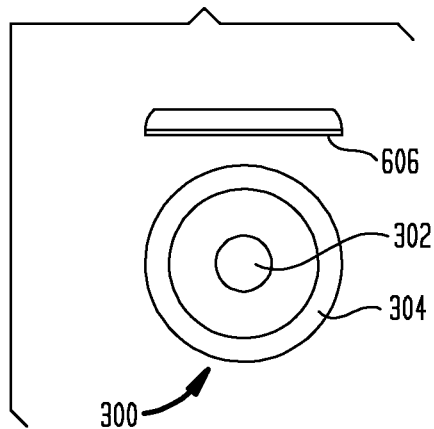
FIG. 6A is a bottom and side view of the one-piece device showing the application of an elastomeric coating to the bottom surface in accordance with a further embodiment of the present invention.
Figure 6B:
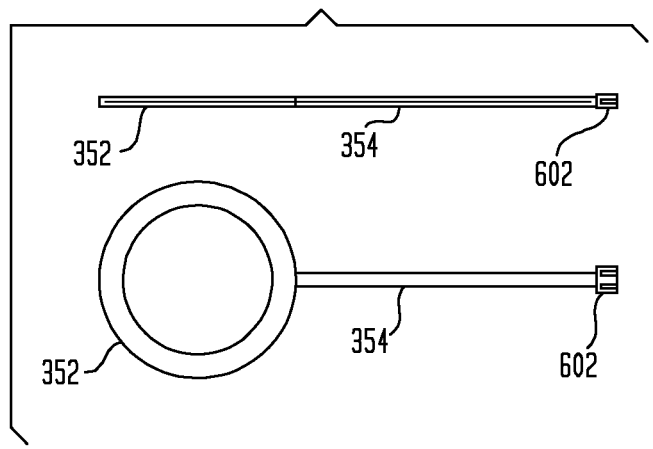
FIG. 6B is a bottom and side view of the thin flexible coil assembly showing the application of an elastomeric coating over all surfaces in accordance with a further embodiment of the present invention.
Figure 6C:
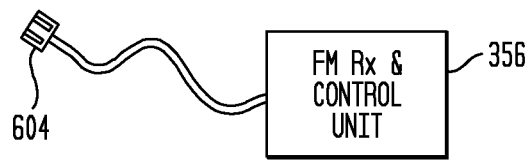
FIG. 6C is a conceptual view of the receiver module (FM receiver/control unit) for use with the flexible coil assembly in accordance with a further embodiment of the present invention.

FIG. 6A is a side and bottom view of alert system 300 illustrated in FIG. 3A. Similarly, FIG. 6B is a side and bottom view of coil 352 and lead 354 of alert system 350 illustrated in FIG. 3B. In the embodiment illustrated in FIG. 6B, coil 352 and lead 354 are coated with an elastomeric coating material to impart 'stickiness' and durability to the coil. An in-line connector 602 is located at the end of lead 354 to facilitate connection to FM receiver/control unit 356 (FIG. 6C).

In the embodiment illustrated in FIG. 6A an elastomeric coating 606 has been applied to the bottom surface of alert device 300. The elastomeric material can include dimples, protrusions and the like, to improve retention onto the recipient's head by way of increasing friction at this interface. The elastomeric coating 606 may increase the distance of the coil from the head by approximately 1 mm.

This magnetic fixation scheme can be significantly augmented by the application of a non-slip elastomeric coating 606 on the bottom surface of the coil, preventing small disturbances, such as rolling the head on a pillow, from dislodging the coil.

By improving the retention of the transmitting coil on the recipient's head, the magnetic holding force can be reduced, thus reducing the weight of the coil by using smaller magnets. This also provides an improved comfort level for the recipient.

A variety of elastomeric coating materials are available and the choice of material depends on the final design parameters of the device (compatibility with the substrate, durability, color, feel etc.). The following materials would be suitable: Kraton TPC having a hardness in the range of Shore A 15 to Shore A 50; Santoprene TPV having a hardness in the range of Shore A 30 to Shore A 50' Nitrile rubber NRB having a hardness in the range of Shore A 30 to Shore A 50; and Silicone Rubber having a hardness in the range of Shore A 30 to Shore A 50.

Some recipients may find it preferable to use a head band in conjunction with the one piece magnetically attached device. Alternatively the coil could be built into the headband.

Figure 7A:
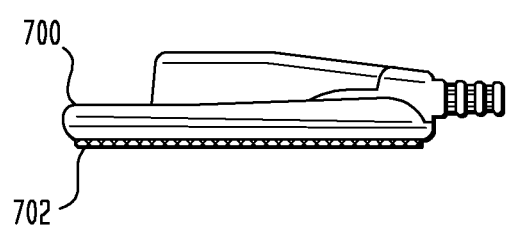
FIG. 7A is a side view of a transmission coil with an elastomeric coating in accordance with a further embodiment of the present invention.
Figure 7B:
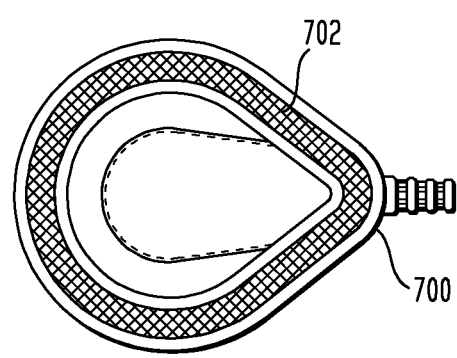
FIG. 7B is a bottom view of the transmission coil of FIG. 7A in accordance with a further embodiment of the present invention.

It is noted that the elastomeric coating can also be applied to a traditional transmission coil, as shown in FIGS. 7A and 7B. FIG. 7A is a side view and FIG. 7B is a bottom view of an embodiment of external coil 130 illustrated in FIG. 1, referred to herein as external coil 700. External coil 700 has an elastomeric coating 702 applied to the surface that abuts a recipient's skull. In this embodiment, elastomeric coating 702 is applied around the perimeter of the entire device. It should be appreciated, however, that elastomeric coating 702 may be applied contiguously or non-contiguously around a portion or the entire periphery of the device surface.

Figure 8A:
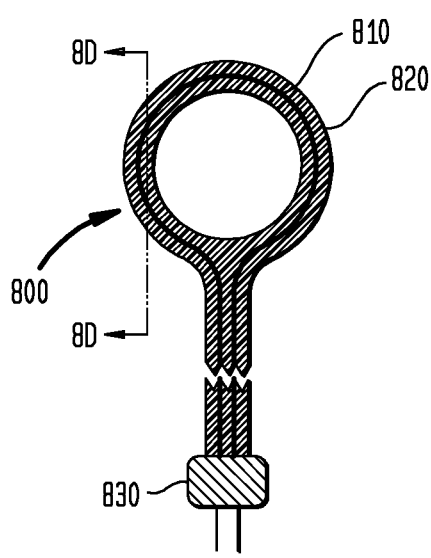
FIG. 8A is a cross-sectional plan view of an alert system transmission coil in accordance with one embodiment of the present invention.
Figure 8B:
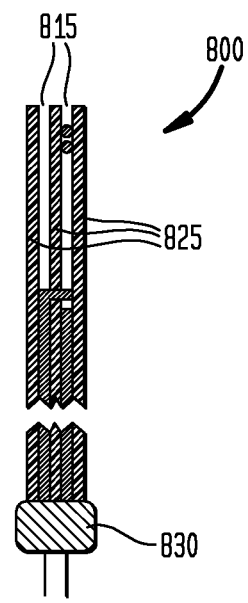
FIG. 8B is a cross-sectional side view of the transmission coil illustrated in FIG. 8A.
Figure 8C:
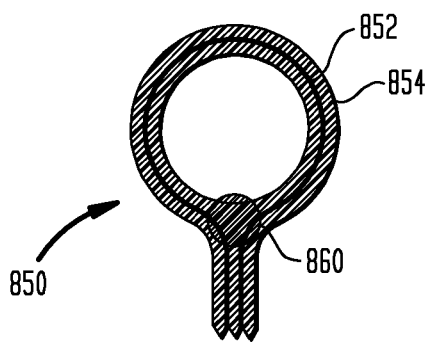
FIG. 8C is a top cross-sectional view of an alert system transmission coil in accordance with another embodiment of the present invention.
Figure 8D:
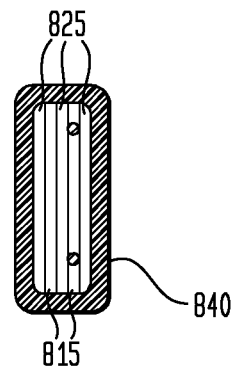
FIG. 8D is a side view of a side view of an encapsulated coil in accordance with a further embodiment of the present invention.

Embodiments of a thin transmission coil is described next below with reference to FIGS. 8A through 8D. FIG. 8A is a cross-sectional plan view of an alert system transmission coil in accordance with one embodiment of the present invention. FIG. 8B is a cross-sectional side view of the transmission coil illustrated in FIG. 8A. FIG. 8C is a top cross-sectional view of an alert system transmission coil in accordance with another embodiment of the present invention. FIG. 8D is a side view of a side view of an encapsulated coil in accordance with a further embodiment of the present invention.

In FIGS. 8A and 8B one embodiment of a thin transmission coil 800 is illustrated. Transmission coil 800 is similar to the transmission coil embodiments described above with reference to FIGS. 6A and 6B.

Thin transmission coil 800 comprises a conductive coil 810 disposed between one or more layers 825 of an insulating carrier 820. In the embodiment illustrated in FIG. 8B, there are three (3) insulating layers 825 defining two conductor layers 815. In one embodiment, conductor layers 815 may be formed of copper and approximately 0.1 mm thick. In the same or other embodiment, insulating layers 825 are formed of, for example, polyimide, and are approximately 0.1 mm thick. The total thickness of the illustrative embodiment of coil 800 is approximately 0.5 mm. It should be appreciated that conductor layers 815 may have a different thickness and need not be of consistent thickness. Similarly, it should be appreciated that insulating layers 825 may have a different thickness and need not be of consistent thickness.

Thin transmission coil 800 may be implemented for use with a tight fitting headgear, such as ski, cycle and motorbike helmets. Such a transmission coil 800 may be manufactured using standard PCB fabrication techniques, which are well-known to those of ordinary skill in the art. In one embodiment, transmission coil 800 is approximately 30 mm in diameter, although transmission coil 800 may have any dimensions appropriate for the particular application.

In FIG. 8C, an embodiment of an active transmission coil 850 is illustrated. Active transmission coil 850 comprises a conductive coil 852 disposed between one or more layers of an insulating carrier 854, and surface mount components 860. Surface mount components 860 are encapsulated in an epoxy or other suitable non-electrically conductive material. In one embodiment, surface mount components 860 adds approximately 0.8 mm to the total thickness of transmission coil 850. Further, either version of transmission coil 800, 850 may be overmolded with an elastomer. For example, FIG. 8D is a cross-sectional side view of one embodiment of transmission coil 800 illustrated in FIG. 8A, for example santoprene, which adds approximately 0.5 mm to the thickness.

Figure 9:
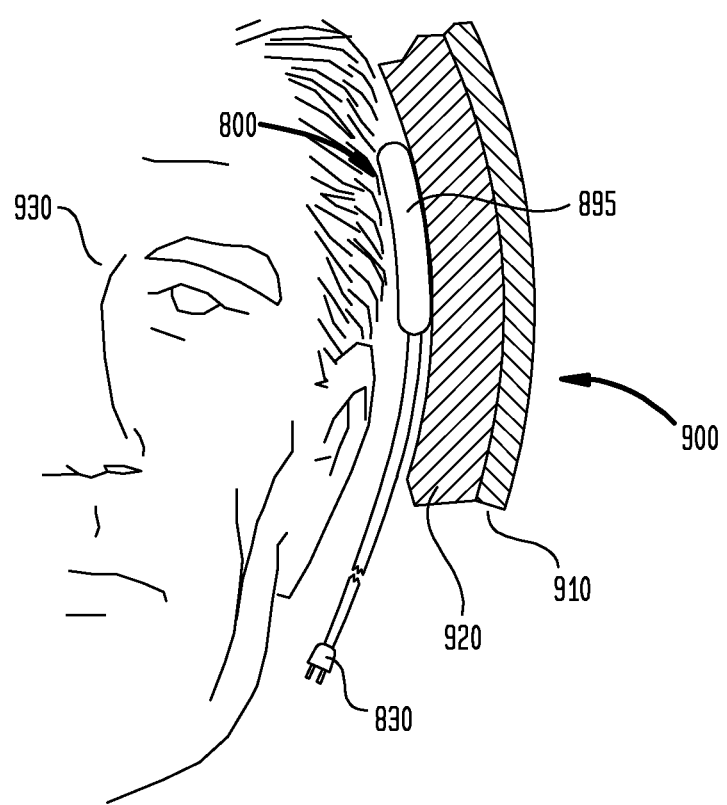
FIG. 9 is a cross-sectional view of the transmission coil illustrated in FIGS. 8A and 8B fixedly secured to an interior surface of a helmet.

FIG. 9 is a cross-sectional view of transmission coil 800 positioned inside a helmet 900. Helmet 900 comprises a rigid cover 910 over a shock-absorbing material 920. Hitherto, while "compression" helmets offer the most protection, the tightness of the fit tends to dislodge conventional transmitter coils off the recipient's head every time the helmet is worn. Further, it is not desirable to alter the padding of such helmets to accommodate the coil, as this usually voids the warranty of the helmet.

In the embodiment shown in FIG. 9, an exemplary transmission coil of the present invention, such as transmission coil 800, is shown positioned between shock-absorbing material 920 of helmet 900 and the head 930 of the recipient. In this embodiment, transmission coil 800 is a flexible PCB as descried above with reference to FIGS. 8A and 8B, with a flexible overmolding 840 as described above with reference to FIG. 8D. This makes coil 800 flexible and allows a better fit between head 930 and helmet 900. Moreover, this advantageously ensures there is no danger of coil 800 causing injury during an impact to helmet 900.

A thickness less than 2 mm is achievable, particularly given that there is no requirement for a retaining magnetic, which is usually the thickest part of a conventional transmission coil. Preferably, connector plug 830 is placed remote from the coil 800 attached by a short length of cable.

Transmission coil 800 may be fixed in position to the inside of the protective headgear 900 as shown in FIG. 9 by, for example, glue 895. As one of ordinary skill in the art would appreciate, fixation means 895 may be, for example, Velcro, stitching, and the like in alternative embodiments of the present invention. The thin coil option is less expensive to manufacture than current transmission coils. Hence if more than one helmet was used for different sports, a different coil 800 may be supplied for each helmet 900.

Although the present invention has been principally described with reference to a cochlear implant, it will be appreciated that this construction can readily be applied to ABIs, other medical devices where a coil is implanted in the head e.g. vision systems, deep brain stimulation (e.g. for Parkinsons treatment), Middle ear implants (DACS), or other prosthetic hearing implant now or later developed.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the invention as shown in the specific embodiments without departing from the spirit or scope of the invention as broadly described. For example, the coil described in combination with a headband or helmet could also be used by a cochlear implant recipient who has had the implant magnet removed. Removal of the implant magnet is a feature offered by some cochlear implants to facilitate MRI scans. The present embodiments are, therefore, to be considered in all respects as illustrative and not restrictive.

Any discussion of documents, acts, materials, devices, articles or the like which has been included in the present specification is solely for the purpose of providing a context for the present invention. It is not to be taken as an admission that any of these matters form part of the prior art or were common general knowledge in the field relevant to the present invention as it existed before the priority date of each claim of this application.

What is claimed is:

1. An alert system for use in a prosthetic hearing implant comprising:
   an event detection module comprising at least one microphone and a transmitter configured to transmit a signal representative of received audio signals; and
   a wearable alarm module configured to receive and analyze one or more characteristics of the representative signal to determine whether an alarm event has been detected, and configured to transmit a specific stimulation signal to an implanted component of the prosthetic hearing implant when the alarm event has been detected.

2. The alert system of claim 1, wherein the specific stimulation signal steadily increases an amplitude of stimuli over a series of bursts.

3. The alert system of claim 2, wherein the wearable alarm module is configured to transmit the specific stimulation signal as a predefined data sequence.

4. The alert system of claim 3, wherein the alert system is adapted for use with a cochlear implant, and the specific stimulation signal corresponds to any one of an instruction to apply a constant amplitude stimulus sequence to an electrode, an instruction to sequentially apply a sequence of pulses to a group of predefined electrodes, or an instruction to apply a sequence stimulation with a steady increase in the amplitude of the stimulation to at least one electrode.

5. The alert system of claim 1, wherein said received audio signal is selected from the group comprising one or more of a phone ring, an alarm clock, a smoke alarm, a doorbell, an intruder alarm, a baby monitor, or a sound having greater than a predetermined level.

6. The alert system of claim 1, wherein the event detection module is configured to transmit the signal representative of the received audio signal by electrical, electronic or radio means.

7. The alert system of claim 1, wherein the wearable alarm module comprises:
   a helmet adapted to be worn on the recipient's head, the helmet comprising a rigid cover over a shock-absorbing material; and
   a transmission coil positioned inside the helmet and configured to transmit the specific stimulation signal to the implanted component of the prosthetic hearing implant.

8. The alert system of claim 7, wherein the transmission coil is a flexible printed circuit board and the transmission coil further comprises:
   a flexible overmolding secured to the surface of the flexible printed circuit board.

9. The alert system of claim 1, wherein the specific stimulation signal comprises a constant amplitude stimulus sequence directed towards one active electrode of the implanted component.

10. The alert system of claim 1, wherein the specific stimulation signal comprises a sequence of pulses applied sequentially to a group of electrodes of the implanted component.

11. The alert system of claim 1, wherein:
the wearable alarm module is configured to analyze a characteristic of the representative signal to differentiate the representative signal from another representative signal received from the same source as the representative signal.

12. A household alarm system, comprising:
the alert system of claim 1, wherein the event detection module is configured to detect an event that occurs in the home corresponding to a household alarm.

13. The alert system of claim 1, wherein the wearable alarm does not transmit the specific stimulation signal to the implanted component if the alarm event has not been detected even when the wearable alarm module receives the representative signal.

14. The alert system of claim 1, wherein the wearable alarm module includes a flexible RF coil configured to transcutaneously communicate with the implanted component.

15. The alert system of claim 1, wherein the wearable alarm module is configured to transcutaneously transmit the specific stimulation signal to the implanted component of the prosthetic hearing implant, wherein the implanted component is implanted beneath the skin of a recipient, when the alarm event has been detected.

16. The alert system of claim 1, wherein the wearable alarm module is configured to be worn away from a pinna of a human when transcutaneous transmitting the specific stimulation signal.

17. The alert system of claim 1, wherein the wearable alarm module is configured to receive only RF signals.

18. The alert system of claim 1, wherein the wearable alarm module includes a flexible overmolding containing therein a flexible RF coil configured to transcutaneously communicate with the implanted component.

19. The alert system of claim 1, wherein the wearable alarm module includes a transmission coil in the form of a flexible printed circuit board, wherein the transmission coil is configured to transcutaneously communicate with the implanted component.

20. The alert system of claim 1, wherein the implanted component is a component configured to be permanently implanted in the recipient.

21. The alert system of claim 1, wherein the specific stimulation signal is a signal that activates the implanted component so as to artificially evoke a hearing percept based on the specific stimulation signal in the person in which the implanted component is implanted.

22. The alert system of claim 1, wherein the implanted component is a component configured to be implanted underneath skin of the recipient, and wherein the specific stimulation signal is a signal that activates the implanted component so as to artificially evoke a hearing percept based on the specific stimulation signal in the person in which the implanted component is implanted.

23. A method for detecting an alarm event in an alert system for a prosthetic hearing implant, comprising:
receiving, at a microphone of an event detection module, an audio signal;
analyzing one or more characteristics of a signal representative of the received audio signal to determine whether an alarm event has been detected;
transmitting a specific stimulation signal to an implanted component of the prosthetic hearing implant upon a determination that the alarm event has been detected; and
evoking a hearing percept in the recipient of the prosthetic hearing implant based on the transmitted specific stimulation signal.

24. The method of claim 23, wherein the one or more characteristics comprise one or more of the group consisting of amplitude, frequency, and duration.

25. The method of claim 23, wherein the wearable alarm module is configured to be removably held externally adjacent the prosthetic hearing implant.

26. The method of claim 23, wherein the specific stimulation signal comprises a constant amplitude stimulus sequence directed towards one active electrode of the implanted component.

27. The method of claim 23, further comprising:
determining, as a result of the analysis, that an alarm event has not been detected, and thus not transmitting, by the wearable alarm module, the specific stimulation signal to an implanted component of the prosthetic hearing implant;
subsequently receiving, at a microphone of the event detection module, a second audio signal;
analyzing one or more characteristics of a second signal representative of the received second audio signal in a wearable alarm module to determine whether an alarm event has been detected; and
transmitting, by the wearable alarm module, a specific stimulation signal to an implanted component of the prosthetic hearing implant that the alarm event has been detected based on the analysis of the one or more characteristics of the second signal representative of the received second audio signal.

28. The method of claim 23, wherein:
the alarm event is an event not associated with the prosthetic hearing implant.

29. The method of claim 23, wherein:
the alarm event is one or more of a phone ring, an alarm clock annunciation, a smoke alarm annunciation, a doorbell annunciation, an intruder alarm annunciation, or a baby monitor annunciation.

30. The method of claim 23, wherein:
the actions of analyzing and transmitting occur utilizing a component that is insensitive to sound.

31. The method of claim 23, wherein:
the actions of analyzing and transmitting occur without a body worn microphone being worn on the recipient.

32. The method of claim 23, wherein:
the action of transmitting is executed utilizing a wearable alarm module worn by the recipient completely away from the pinna of the recipient.

33. A method, comprising:
utilizing an implantable component of a hearing prosthesis implanted beneath skin of the recipient to evoke a hearing percept based on first captured sound;
subsequent to evoking the hearing percept based on the first captured sound, receiving at an external component remote from the recipient third signals;
analyzing the third signals and determining that an alarm event has occurred; and upon determining that an alarm event has occurred, evoking a hearing percept in the recipient indicative of an alarm using the implantable component.

34. The method of claim 33, wherein:

upon a determination that the alarm event has not occurred, preventing a hearing percept from being evoked based on the received third signals.

* * * * *